United States Patent [19]
Schierholz et al.

[11] Patent Number: 6,140,090
[45] Date of Patent: Oct. 31, 2000

[54] METHOD FOR THE LABELING OF MOLECULES

[75] Inventors: Bernd Schierholz, Hamburg; Günter Bauer, Schmalfeld; Irmgard Werner, Neu Wulmstorf; Franz-Josef Meyer-Almes, Iserlohn; Oliver Kreuzer, Berlin, all of Germany

[73] Assignee: Evotec BioSystems AG, Hamburg, Germany

[21] Appl. No.: 09/155,571

[22] PCT Filed: Mar. 29, 1997

[86] PCT No.: PCT/EP97/01600

§ 371 Date: Nov. 4, 1998

§ 102(e) Date: Nov. 4, 1998

[87] PCT Pub. No.: WO97/37221

PCT Pub. Date: Oct. 9, 1997

[30] Foreign Application Priority Data

Apr. 2, 1996 [DE] Germany ............................ 196 12 650

[51] Int. Cl.⁷ .......................... C07K 1/13; G01N 33/533; G01N 33/535; G01N 33/543

[52] U.S. Cl. .......................... 435/188; 422/239; 436/166; 530/391.3; 530/395; 530/402; 536/1.11; 536/22.1

[58] Field of Search ........................... 422/239, 68.1, 422/82.08, 221, 311; 424/9.6, 9.61, 1.25; 435/7.1, 7.5, 7.6, 7.7, 7.71, 7.72, 7.9, 188, 287.1, 287.2, 287.9; 436/17, 166, 543, 544, 545, 546, 547, 548, 807, 808, 809, 810; 530/334, 391.3, 391.5, 391.7, 391.9, 395, 402, 403, 404, 405, 406; 536/1.11, 22.1, 23.1, 26.41, 26.6

[56] References Cited

U.S. PATENT DOCUMENTS

| | | | |
|---|---|---|---|
| 4,816,513 | 3/1989 | Bridgham et al. | 525/54.11 |
| 4,874,813 | 10/1989 | O'Shannessy | 525/54.1 |
| 5,102,986 | 4/1992 | Coffey et al. | 530/334 |
| 5,244,816 | 9/1993 | Subramanian | 436/545 |
| 5,252,496 | 10/1993 | Kang et al. | 436/529 |
| 5,290,925 | 3/1994 | Fino | 536/25.32 |
| 5,318,680 | 6/1994 | Fishman et al. | 204/180.1 |
| 5,334,538 | 8/1994 | Parker et al. | 436/525 |
| 5,479,937 | 1/1996 | Thieme et al. | 128/760 |
| 5,705,610 | 1/1998 | Zuckermann et al. | 530/338 |
| 5,766,933 | 6/1998 | El Shami et al. | 435/287.2 |

FOREIGN PATENT DOCUMENTS 39 12046 A1  3/1990  Germany.

*Primary Examiner*—Jeffrey E. Russel
*Attorney, Agent, or Firm*—Jacobson, Price, Holman & Stern, PLLC

[57] ABSTRACT

A method for the labeling of molecules through the reaction of molecules to be labeled with labels at a solid phase (matrix), characterized in that the molecules enter a reaction chamber in which a matrix loaded with a reactive component is provided, and after the coupling has taken place, the labeled molecules leave the reaction chamber through a porous means.

15 Claims, No Drawings

METHOD FOR THE LABELING OF MOLECULES

The present invention relates to a method for the labeling of molecules and a device for performing the method.

The modification of proteins, polycarboxylic acids and other biopolymers by labeling with a reporter molecule which may be luminescent, in particular, is of great importance to many fields of applications, such as immunology, cellular biology or the examination of molecular interactions such as those occurring, for example, between ligands and receptors, or proteins and nucleic acids. The use of fluorescence-labeled molecules is not limited to the performance of assays. Fluorescence-labeling does not only gain importance to the extent to which radioactive assay methods become fewer. The labeled substances are employed in fluorescence-immunological assays (e.g., ELISA) or in various fluorescence techniques, such as fluorescence microscopy, fluorescence polarization and fluorescence life measurements, or fluorescence correlation spectroscopy.

Methods for the fluorescence-labeling of biopolymers have been known. Thus, it is possible to couple reactive dyes, such as the sulfonyl chloride derivative of sulforhodamine 101 (Texas Red®), covalently to amino groups of the protein by directly adding them to a protein solution. However, one disadvantage is the rapid hydrolysis of the reactive dye in aqueous solution at room temperature since the dye molecules are prematurely inactivated before reacting as desired with the molecules to be labeled. Thus, such coupling reactions are preferably performed at 4° C. (Molecular Probes MP 353 Dec. 21, 1993). The coupling times are between one and four hours depending on the reactive dye chosen and the protein concentration (Titus et al., Journal of Immunological Methods, 50, 193–204, 1992). Rinderknecht (Experentia 16, 430, 1960) describes another fluorescence-labeling procedure using Celite adsorbed fluorescent dyes which are added to the solution containing the substances to be labeled. By providing the fluorescent dyes on such an increased surface area, coupling times of 30 minutes can be achieved. After the reaction, the Celite material is separated off by centrifugation.

In particular, the above mentioned methods have a drawback in that the performance of the methods requires a person skilled in dealing with hydrolysis-sensitive substances and an equipment for preventing health hazards, such as an exhaust hood. In addition, it has been found disadvantageous that the reproducibility of the methods is highly dependent on accidental circumstances, such as the skill of those performing the reaction.

The object of the invention has been to provide an industrially applicable method for the labeling, especially fluorescence-labeling, of molecules which can be reproducibly performed by unskilled persons or automatically.

The object of the invention is achieved by a method for the labeling of molecules by reacting the molecules in a reaction chamber in which a solid phase (matrix) loaded with a reactive component is provided, and after the coupling has taken place, the labeled molecules leave the reaction chamber through a porous means; and a device having a cavity, in the lumen of which at least one porous means and a matrix loaded with a reactive component are provide, for performing the method according to the invention.

The method according to the invention is characterized in that the molecules to be labeled enter a reaction chamber in which a matrix loaded with a reactive component is provided, and after the coupling has taken place, the fluorescence-labeled molecules leave the reaction chamber through a porous means.

The labeling reaction is preferably a fluorescence-labeling reaction. The method according to the invention is also advantageously suitable for the labeling with various other reagents or substances which are detectable as such or contain a detectable portion. Thus, according to the invention, the labeling may be done with haptens which are susceptible to immunological detection. Similarly, the method according to the invention may also be employed for biotinylation so that detection with streptavidin or avidin can be performed later.

The labeled molecules' leaving the reaction chamber may be effected, for example, by (hydrostatic) pressure, reduced pressure or centrifugation.

The molecules to be labeled may enter the reaction chamber through a porous means in the same way as the labeled molecules leave the reaction chamber.

A matrix of inorganic materials, such as kieselguhr of different grain sizes, for example, Celite®, has proven particularly suitable for use in the method according to the invention.

The molecules to be labeled are preferably substances having a reactive amino, thiol and/or aldehyde group. However, carboxy groups may also be labeled with suitable amine dyes after reaction with carbodiimides (M. Brinkley, Bioconjugate Chem., 3, 2–13, 1992). It is particularly preferred that the substances to be labeled are natural or synthetic oligo- or polymers, such as proteins, especially antibodies or enzymes, nucleic acids, carbohydrates, polycarboxylic acids and glycoproteins.

The reactive components are preferably amino-reactive reagents, such as fluorescent isothiocyanate derivatives, especially fluorescein isothiocyanate or tetramethylrhodamine isothiocyanate, sulfonyl chloride derivatives, e.g., of sulforhodamine 101, or fluorescent derivatives of reactive esters, such as N-hydroxysuccinimidyl ester (NHS). Corresponding biotin or hapten derivatives may also be used according to the invention. Thiol-reactive reagents may also be employed according to the invention, especially fluorescent derivatives of haloacetamides or maleinimidyl derivatives. Further, carboxy- or aldehyde-reactive reagents, such as amine dyes or hydrazides, may also be used in the method according to the invention (M. Brinkley, Bioconjugate Chem., 3, 2–13, 1992).

The average pore size of the porous means should be selected according to the size of the molecules to be labeled. The pore size is preferred to be between 50 $\mu$m and 100 $\mu$m and is particularly preferred to be between 70 $\mu$m and 90 $\mu$m. The thickness of the porous means should preferably be adapted to the system to be labeled. A thickness of <2 mm has proven advantageous. In particular, the porous means consists of a biocompatible inert frit material, preferably of polyethylene. Advantageously, as compared to the prior art, a preliminary purification occurs by the labeled molecules' leaving the reaction chamber through the porous means.

The temperature for performing the method according to the invention should preferably be adapted to the system to be labeled. Suitable temperature ranges for the particular labeling reaction can be determined by preliminary experiments. Thus, parallel experiments, such as the preparation of the Texas Red®/alcaline phosphatase conjugate, at different temperatures have shown that the optimum temperature of this labeling reaction is at 24° C. With more sensitive substances, however, it may be advisable to perform the method according to the invention at lower temperatures, especially at 4° C.

The method according to the invention is suitable for achieving a predetermined degree of labeling in a simple way. "Degree of labeling" means the number of covalently coupled labeling molecules per labeled molecule.

This will be illustrated in the Example below for the preparation of conjugates by the reaction of resorufin-NHS with thyroglobulin. In parallel experiments, given amounts of resorufin-NHS coupled to a Celite matrix were respectively charged to individual reaction chambers, and increasing amounts of thyroglobulin were added. Thus, according to the invention, degrees of labeling of between 5 and 22 can be achieved in the case according to Example 1. Similarly, different degrees of labeling of alkaline phosphatase could be achieved in coupling reactions using Texas Red /sulfonyl chloride, fluorescein/isothiocyanate (FITC), tetramethylrhodamine/isothiocyanate (TRITC), succinimidyl esters, such as BODIPY 581/591 (Molecular Probes), iodoacetamides, such as tetramethylrhodamine iodoacetamide (TMR-IA), and tetramethylrhodamine maleinimide. By appropriately selecting the ratio of reactive component to the substance to be labeled, any degree of labeling of <5 could be adjusted as desired, e.g., in the Texas Red®/lactalbumin coupling reaction. Other proteins, such as apoferritin and lysozyme, could also be reproducibly labeled in a simple way, e.g., using Texas Red®/sulfonyl chloride. Similarly, antibodies (rabbit IgG) could be labeled by the method according to the invention using FITC, TRITC and the succinimidyl esters of resorufin and tetramethylrhodamine.

The method according to the invention is also suitable for the labeling of oligonucleotides. By way of example, a 40mer oligonucleotide 5'-modified with $NH_2$ was labeled using rhodamine Green®/NHS (coupling buffer; 0.1 M Na carbonate buffer, pH 10.5; 100fold molar excess of dye).

In a further Example, the method according to the invention was employed for the biotinylation of alkaline phosphatase using biotin N-hydroxysuccinimidyl ester as the reactive component.

Another advantage of the method according to the invention is its capability of being quickly performed. The coupling times which have been necessary in the prior art can be significantly reduced to a few seconds using the method according to the invention.

Measurements of enzyme activity, e.g., of alkaline phosphatase, showed that the conjugates prepared using Texas Red /sulfonyl chloride in the method according to the invention exhibit an activity which is reduced by only a few percent as compared to the native enzyme.

The method according to the invention can be performed by means of a device according to claim 10 which has an essentially cylindrical cavity in the lumen of which at least one porous means and a matrix loaded with a reactive component are provided. Preferably, however, there are two porous means in the lumen between which the matrix loaded with the reactive component is arranged. According to the invention, the device can be, in particular, a syringe made of an inert material and having different capacities. Polypropylene is preferably used as a biocompatible inert syringe material.

In a preferred embodiment of the device according to the invention, the pore size of the porous means is between 50 $\mu$m and 100 $\mu$m, preferably between 70 $\mu$m and 90 $\mu$m.

Preferably, a matrix consisting of inorganic materials, such as kieselguhr of different grain sizes, is employed.

The device according to the invention is characterized by its storage stability. Syringes suitably stored for up to 455 days according to Example 6 showed no significant deterioration of the labeling reaction as compared to syringes immediately used after having been filled with Texas Red®/sulfonyl chloride/Celite® for the labeling of alkaline phosphatase.

EXAMPLE 1

Preparation of a device for performing the method according to the invention

The piston of a syringe made of polypropylene was removed, and the outlet of the syringe was provided with a porous means made of polyethylene the diameter of which was adapted to the inner diameter of the syringe cavity. The thickness of the porous means was 2 mm, and its average pore size was 80 $\mu$m. Together with another similar porous means, the piston and the related syringe were dried at 50° C. until about half an hour before use. 20 mg of Celite® was weighed into a rotary evaporator pear-shaped distilling flask. The pear-shaped distilling flask charged with Celite® was placed in a desiccator together with the porous means, the flask and the above prepared syringe, and a vacuum was drawn. Thereafter, the desiccator was flooded with argon, and with the lid being half-opened, argon was permanently supplied through a flexible tube reaching to the bottom of the desiccator. A desired amount, e.g., 0.1 mg, of Texas Red®/sulfonyl chloride was dissolved in chloroform in the desiccator and then completely transferred onto the Celite®. The desiccator was closed, and a vacuum was drawn for about half an hour. Prior to further processing, the Celite® matrix loaded with Texas Red®/sulfonyl chloride was left in the desiccator for another two hours. The filling of the syringe was performed in the desiccator. To this end, the latter was again flooded with argon, and with the lid being half-opened, argon was permanently supplied through a flexible tube reaching to the bottom of the desiccator. The Celite® matrix loaded with the Texas Red®/sulfonyl chloride reactive component was filled into the syringe. A second porous means was subsequently inserted into the syringe. When the syringe piston was operated, care was taken that the Celite® matrix loaded with Texas Red®/sulfonyl chloride, which was thus located between two porous means, was but slightly compressed. However, it is also possible to dispense with the second porous means which bounds the space for the dye/Celite® complex in the syringe. After the syringe piston has been inserted, the reaction space within the syringe can be varied by displacing the piston.

EXAMPLE 2

Labeling of thyroglobulin with different degrees of labeling

In parallel experiments, 210 nmol each of resorufin-NHS coupled to a Celite® matrix was respectively filled in individual reaction chambers, and there was added 100 $\mu$l each of a coupling buffer (0.1 M Na borate buffer, pH 9.0) containing a) 7.1 mg of thyroglobulin (corresponding to a 20fold molar excess of dye), b) 3.6 mg of thyroglobulin (corresponding to a 40fold molar excess of dye), c) 1.42 mg of thyroglobulin (corresponding to a 100fold molar excess of dye), d) 0.71 mg of thyroglobulin (corresponding to a 200fold molar excess of dye), and e) 0.36 mg of thyroglobulin (corresponding to a 400fold molar excess of dye). The reaction chambers were rinsed four times with 100 $\mu$l each of coupling buffer, and the eluate was added to the respective first eluate. The total eluate was purified by chromatography in a per se known manner. The concentrations of the biomolecule and of the dye in the conjugate solution were determined spectroscopically in a per se known manner through the molar extinction coefficient.

The following degrees of labeling were achieved:

| molar excess of dye during the reaction | degree of labeling |
|---|---|
| 20 | 6.2 |
| 40 | 8.8 |
| 100 | 20 |
| 200 | 22 |
| 400 | 22 |

EXAMPLE 3
Labeling of alcaline phosphatase with Texas Red® sulfonyl chloride 50 µl of the enzyme solution (10 mg of alkaline phosphatase per ml of coupling buffer) were added to a 1.5 ml Eppendorf® tube and mixed with 50 µl of coupling buffer (0.1 M Na borate buffer, pH 9.0) which had been preliminarily brought to a temperature of 24° C. An injection cannula was placed onto the device, i.e., a syringe in this case, and used to draw the enzyme solution into the device; the solution was shortly mixed by moving the piston, and the eluate was added to an Eppendorf® tube kept on ice. The device was then rinsed four times with 100 µl of coupling buffer, and the eluate was added to the respective Eppendorf® tube. The total eluate was purified by chromatography in a per se known manner.

EXAMPLE 4
Labeling of antibodies

Using Celite® matrices loaded with FITC and the succinimidyl esters of Texas Red®, resorufin and tetramethylrhodamine (about 200 nmol of dye per device), rabbit IgG was labeled in the device according to the invention. 2.8 mg of antibody was first dissolved in 200 µl of 0.1 M Na borate buffer (pH 9.0). Then, 30 µl of this solution was mixed with 70 µl of 0.1 M Na borate buffer. An injection cannula was placed onto the device, i.e., a syringe in this case, and used to draw the antibody solution into the device; the solution was shortly mixed by moving the piston, and the eluate was added to an Eppendorf® tube kept on ice. The device was then rinsed four times with 100 µl of coupling buffer, and the eluate was added to the respective Eppendorf® tube. The total eluate was purified by chromatography in a per se known manner. Degrees of labeling of 7.0 (FITC), 7.7 (resorufin-NHS), 1.8 (tetramethylrhodamine succinimidyl ester) and 0.7 (TRITC) were achieved.

EXAMPLE 5
Biotinylation of alkaline phosphatase

100 µl of the enzyme solution (10 mg of alkaline phosphatase per ml of 0.1 M Na borate buffer, pH 9.0) was labeled much in the same way as in Example 3 using biotin-NHS as the reactive component.

EXAMPLE 6
Storage Stability

Syringes filled with Texas Red®/sulfonyl chloride/Celite® were individually packaged in Barr-O-Nit® flat bags using an impulse spot welder, and stored at −20° C. After 7, 13, 21, 27, 41, 76 and 455 days of storage, the syringes were used for the labeling of alkaline phosphatase. The degrees of labeling were determined and compared to the degree of labeling achieved with a syringe used for the labeling of alkaline phosphatase immediately after having been filled with Texas Red®/sulfonyl chloride/Celite®.

| Storage time (days) | Degree of labeling |
|---|---|
| 0 | 2.3 |
| 7 | 2.2 |
| 13 | 1.9 |
| 21 | 2.2 |
| 27 | 2.1 |
| 41 | 2.2 |
| 76 | 2.1 |
| 455 | 2.3 |

What is claimed is:

1. A method for labeling molecules through the reaction of molecules to be covalently labeled with labels at a matrix, characterized in that said molecules enter a reaction chamber in which a matrix loaded with a reactive component is provided, and after coupling has taken place, the labeled molecules leave the reaction chamber through a porous means.

2. The method according to claim 1, wherein said labeling is fluorescence-labeling, biotinylation and/or hapten labeling.

3. The method according to claim 1, wherein fluorescence-labeled molecules' leaving the reaction chamber is effected by pressure or centrifugation.

4. The method according to claim 1, wherein the molecules to be labeled enter the reaction chamber through a porous means.

5. The method of claim 1, wherein inorganic materials are used as the matrix.

6. The method according to claim 5, wherein the inorganic materials are comprised of kieselguhr of different grain sizes.

7. The method according to claim 1, wherein the molecules to be labeled have at least one nucleophilic or electrophilic group.

8. The method of claim 7, wherein the nucleophilic or electrophilic group is an amino, thiol and/or aldehyde group.

9. The method according to claim 1, wherein the molecules to be labeled are natural or synthetic oligomers or polymers.

10. The method of claim 9, wherein molecules to be labeled are proteins.

11. The method of claim 10, wherein the proteins are antibodies, enzymes, or glycoproteins.

12. The method according to claim 1, wherein said reactive component is a fluorescent derivative of isothiocyanates, sulfonyl chlorides, N-hydroxysuccinimidyl esters, haloacetamides or maleninimides.

13. The method according to claim 1, wherein the pore size of said porous means is between 50 µm and 100 µm.

14. The method of claim 13, wherein said pore size is between 70 µm and 90 µm.

15. The method of claim 9, wherein the molecules to be labeled are nucleic acids, carbohydrates, or polycarboxylic acids.

* * * * *